United States Patent
Li et al.

(10) Patent No.: US 11,701,599 B2
(45) Date of Patent: Jul. 18, 2023

(54) CONTROL METHOD FOR RECTIFICATION AND PURIFICATION SYSTEM OF ELECTRONIC-GRADE CHLORINE TRIFLUORIDE

(71) Applicant: FUJIAN DEER TECHNOLOGY CO., LTD., Longyan (CN)

(72) Inventors: Xiang Ru Li, Longyan (CN); Jia Lei Li, Longyan (CN); Shi Hua Chen, Longyan (CN); Li Ming Shen, Longyan (CN); Rui Jie Yu, Longyan (CN); Qiang Wu, Longyan (CN)

(73) Assignee: FUJIAN DEER TECHNOLOGY CO., LTD., Longyan (CN)

( * ) Notice: Subject to any disclaimer, the term of this patent is extended or adjusted under 35 U.S.C. 154(b) by 0 days.

(21) Appl. No.: 17/787,336

(22) PCT Filed: Oct. 28, 2021

(86) PCT No.: PCT/CN2021/126903
§ 371 (c)(1),
(2) Date: Jun. 20, 2022

(87) PCT Pub. No.: WO2022/160820
PCT Pub. Date: Aug. 4, 2022

(65) Prior Publication Data
US 2023/0138541 A1    May 4, 2023

(30) Foreign Application Priority Data

Jan. 29, 2021 (CN) .......................... 202110127961.9

(51) Int. Cl.
*B01D 3/14*   (2006.01)
*B01D 3/42*   (2006.01)
*B01D 3/32*   (2006.01)

(52) U.S. Cl.
CPC .............. *B01D 3/143* (2013.01); *B01D 3/322* (2013.01); *B01D 3/42* (2013.01)

(58) Field of Classification Search
CPC .......... B01D 3/14; B01D 3/143; B01D 3/322; B01D 3/42

USPC ...................................................... 423/240 R
See application file for complete search history.

(56) References Cited

U.S. PATENT DOCUMENTS

2019/0046917 A1    2/2019    Yao et al.

FOREIGN PATENT DOCUMENTS

| CN | 104555927 A | 4/2015 |
| CN | 105347307 A | 2/2016 |
| CN | 109772108 A | 5/2019 |
| CN | 111704109 A | 9/2020 |
| CN | 112919419 A | 6/2021 |

OTHER PUBLICATIONS

International Search Report issued in corresponding International application No. PCT/CN2021/126903, dated Jan. 25, 2022.
Written Opinion of the International Search Authority in corresponding International application No. PCT/CN2021/126903.
Chen Yanshan's overview of the research progress of chlorine trifluoride "Low Temperature and Special Gas" Dec. 31, 2020(Dec. 31, 2020) Issue 6 vol. 38 pp. 1-4.

*Primary Examiner* — Edward M Johnson

(57) ABSTRACT

The present disclosure provides a control method for a rectification and purification system of electronic-grade chlorine trifluoride. A rectification device of electronic-grade chlorine trifluoride includes a two-stage cryogenic rectification device including a low-boiling column and a high-boiling column. An extraction agent is arranged in the two-stage cryogenic rectification device for further dissociating associated molecules of hydrogen fluoride and chlorine trifluoride to meet the requirements of electronic-grade chlorine trifluoride. The reflux ratio parameter stability of a vapor-liquid (chlorine trifluoride-hydrogen fluoride) phase equilibrium system can be effectively improved by a column plate temperature control method, thus realizing wide dynamic smooth running under various working conditions. The column plate temperature control method can achieve an effective separation of chlorine trifluoride and various impurity components by deep rectification technology, yielding electronic-grade chlorine trifluoride through purification.

2 Claims, 5 Drawing Sheets

S1, condensing the crude chlorine trifluoride product produced in the reactor 10 by the first Hastelloy-alloy condenser 11 to form a first-stage temperature difference, which thereby provides power for the outlet gas of the reactor 10;

S2, heating the crude chlorine trifluoride product by the first Hastelloy-alloy heating tank 12, so that the liquid inside the tank is vaporized to form a second-stage temperature difference, enabling chlorine trifluoride to quickly reach a saturated vapor pressure to stop self-decomposition;

S3, heating and pressurizing the crude chlorine trifluoride product gas by the Hastelloy-alloy pressure-resistant heating tank 13 to form a third-stage temperature difference, and increasing the internal pressure of the tank to make the chlorine trifluoride gas reach a positive pressure required by subsequent purification processes such as rectification;

S4, conducting cooling and condensation by the liquefaction tank 16 to form a fourth-stage temperature difference, so that the chlorine trifluoride gas from the outlet of the rectification column is condensed into a liquid state for collection and storage.

FIG. 2

S5, the alkali metal adsorbent of the three-stage metal adsorbent bed 14 is heated and associated with hydrogen fluoride to form stronger hydrogen bonds for separation, so as to achieve a first-stage purification. The alkali metal adsorbent is a mixture of NAF, LiF, and $NaHF_2$.

S6, the associated molecules of hydrogen fluoride and chlorine trifluoride are further disassociated by the two-stage cryogenic rectification device 15 to achieve a second-stage purification. The two-stage cryogenic rectification device 15 includes a fluoroether oil extraction agent.

FIG. 3

S7, the temperature of the second-layer column plate at the upper end of the first reboiler is controlled to be 10°C to 12°C, and the temperature of the second-layer column plate at the lower end of the first condenser is controlled to be -22.5°C to 24°C.

S8, the temperature of the upper end of the second reboiler is controlled to be 11°C to 12°C, and the temperature of the lower end of the second condenser is controlled to be -6°C to -4°C.

FIG. 4

CONTROL METHOD FOR RECTIFICATION AND PURIFICATION SYSTEM OF ELECTRONIC-GRADE CHLORINE TRIFLUORIDE

CROSS-REFERENCE TO RELATED PATENT APPLICATIONS

This application is a national stage entry of International Application No. PCT/CN2021/126903, filed on Oct. 28, 2021, which is based upon and claims priority to Chinese Patent Application No. 202110127961.9, filed on Jan. 29, 2021, which is incorporated by reference herein in its entirety.

TECHNICAL FIELD

The present disclosure relates to a control method for a rectification and purification system of electronic-grade chlorine trifluoride.

BACKGROUND

At present, chlorine trifluoride has some special properties such as having a boiling point close to that of hydrogen fluoride and being easily to form a multi-polymer with its impurity system. These special properties increase the difficulty of separation of chlorine trifluoride. As such, it is hard to stably control a concentration of hydrogen fluoride below 500 ppmv using a conventional control method, and difficult to extract electronic-grade chlorine trifluoride through purification.

The prior art Chinese patent application (application number: CN2019112490911, publication number: CN110975315A) discloses an energy-saving rectification and purification system of high-purity propylene oxide, where the middle part of a high-boiling column is fabricated with an inlet for crude propylene oxide, a vapor outlet at the top of the high-boiling column is sequentially connected to a first compressor and a first heat exchanger, the first heat exchanger is connected to a cold material heat exchange pipeline at the bottom of the high-boiling column, a vapor outlet pipeline of the first heat exchanger is sequentially connected to a first throttling valve and a first phase separator and then connected to a first reflux port of the high-boiling column and a feeding port of a low-boiling column, respectively, a vapor outlet of the low-boiling column is sequentially connected to a second compressor and a second heat exchanger, the second heat exchanger is connected to a cold material heat exchange pipeline at the bottom of the low-boiling column, a vapor outlet of the second heat exchanger is sequentially connected to a second throttling valve and a second phase separator and then connected to a reflux port of the low-boiling column and the reflux port of the high-boiling column, respectively. Although the technical solution disclosed by the prior art involves a low-boiling column and a high-boiling column, it is not related to a rectification device for preparing electronic-grade chlorine trifluoride, nor does it elaborate on specific structures of the high- and low-boiling columns or clarify whether an extraction agent is used (Background of the specification of the prior art clearly recites the presence of the following defects: (1) Chemical removal of impurities is conducted by adding hydrazine hydrate and an alkali solvent, which makes it impossible for recycling and reusing of a solvent after purification. (2) Methanol circulating in the process will be converted into methylal due to the presence of the extraction agent, which leads to catalyst poisoning, huge energy consumption during the rectification, and less recycling and severe waste), thus unable to realize the effect of improving the stability of the reflux ratio parameter of a vapor-liquid phase equilibrium system.

Chinese patent application (application number: CN2012101185631, publication number: CN102659508A) discloses a process for separation and refinement of vinyl chloride. Crude vinyl chloride from the compression unit used in a production process of polyvinyl chloride by calcium carbide method is subjected to cooling, dehydration, and deacidification, followed by separation in a rectification device to yield three material streams of light components, refined vinyl chloride, and heavy components, and these three material streams respectively undergo subsequent processes. It is characterized in that: the rectification device is a partitioned column; the three material streams are drawn from the partitioned column from top to bottom, namely, the light component stream is drawn from the top of the column, the refined vinyl chloride monomer is drawn from a part of the column between the top and bottom, and the heavy component stream is drawn from the bottom of the column; a pressure at the top of the partitioned column is 0.3 MPa to 0.7 MPa (absolute pressure), a temperature at the top of the column is 15° C. to 45° C., a pressure at the bottom of the partitioned column is 0.3 MPa to 0.8 MPa (absolute pressure), and a temperature at the bottom of the column is 30° C. to 60° C.

Chinese patent application (application number: CN201310445631x, publication number: CN103694079A) discloses a method for refining and purifying vinyl chloride monomer, including an evaporative condenser, a total condenser, a rectification heat exchanger, an oil-water separator, a vinyl chloride dewatering channel, a pump for feeding first-grade vinyl chloride into low column, a first-stage heat exchanger of low column, a first-stage low-boiling column, a first-stage dephlegmator of low column, a first-stage exhaust condenser, and a first-stage exhaust collector connected in sequence. The outlet of the bottom of the first-stage low-boiling column is provided with a first-stage high-boiling column, a first-stage condenser of high column, a first-stage condenser for finished product, and a first-stage vinyl chloride storage tank connected in sequence. A pump for feeding second-grade vinyl chloride into low column, a second-stage heat exchanger of low column, and a second-stage low-boiling column, etc. are connected in sequence and provided after the first-stage vinyl chloride storage tank.

Chinese patent applications of CN104262082A, CN105481640A, CN109651067A, CN109651110A, CN110240536A, CN211050938U, CN202270376U, CN203355329U, CN209537349U, CN209575807U, CN209940867U, and CN209940868U all relate to the field similar to the present disclosure, but those skilled in the art investigate and suggest that the prior arts mentioned above cannot achieve the effect of stabilizing the reflux ratio parameter of a vapor-liquid (chlorine trifluoride-hydrogen fluoride) phase equilibrium system, and thus cannot realize wide dynamic smooth running under various working conditions nor yield electronic-grade chlorine trifluoride through purification.

For another example, Chinese patent application, with the application number of CN2015108752487 and the publication number of CN105367410A, discloses a hydrorefining system for producing chloroacetic acid. Chinese patent application, with the application number of CN2018114865024 and the publication number of CN109293529A, discloses a purification device and method for producing chlorothalonil where hexachlorobenzene does not exceed 10 ppm. Chinese patent application, with the application number of CN201910990199x and the publication number of CN110590604A, discloses a continuous rectification and purification device for isophthalonitrile. Chinese patent application, with the application number of CN2018220464337 and the publication number of CN209352805U, discloses a purification device for producing chlorothalonil where hexachlorobenzene does not exceed 10 ppm. Although the above-mentioned prior arts are all devices or methods applied in the purification of a certain compound, the technical solutions disclosed above are designed for a specific compound with relatively complicated technical means, and those skilled in the art cannot apply these technical solutions to a rectification and purification system and method for producing electronic-grade chlorine trifluoride according to actual needs. In other words, the above-mentioned prior arts do not give any indication of being able to be applied in a rectification and purification system and method for producing electronic-grade chlorine trifluoride.

In addition, Chinese patent application CN101979364A discloses a preparation method of 2,3,3,3-tetrafluoropropene, CN105111351A discloses a preparation method of a special fluoroether surfactant, and CN105111352A discloses a preparation method of a special fluoroether oligomer. Although in the above-mentioned prior arts, fluoroether oil is adopted in the process of compound preparation, those skilled in the art cannot take a hint from the above contents to apply it in a rectification device of electronic-grade chlorine trifluoride.

For another example, the prior arts of CN101914001A, CN102633597A, CN102701941A, CN103739454A, CN107382682A, CN108103585A, CN109096033A, CN109678668A, CN111217676A, and CN202610130U disclose the use of an extraction agent, a rectification column, and other technical means to extract a compound or a method of compound extraction, but are all silent about the use of an efficient extraction agent and an efficient rectification device. Through experiment and analysis, those skilled in the art believe that the above-mentioned common knowledges are not associated to achieving the effect of effectively improving the stability of the reflux ratio parameter of a vapor-liquid (chlorine trifluoride-hydrogen fluoride) phase equilibrium system by a column plate temperature control method, thus unable to realize wide dynamic smooth running under various working conditions; nor realize the purpose of yielding electronic-grade chlorine trifluoride through an effective separation of chlorine trifluoride and various impurity components by deep rectification technology.

SUMMARY

The present disclosure provides a rectification device of chlorine trifluoride and a method thereof, as well as a purification system and a control method thereof, which can effectively solve the technical problems mentioned in the background.

The technical solutions of the present disclosure are as follows:

A rectification device of electronic-grade chlorine trifluoride, including: a second-stage cryogenic rectification device, wherein the second-stage cryogenic rectification device includes a low-boiling column and a high-boiling column, and an extraction agent is arranged in the second-stage cryogenic rectification device and configured for dissociating associated molecules of hydrogen fluoride and chlorine trifluoride to meet the requirements of electronic-grade chlorine trifluoride.

Preferably, the low-boiling column includes a first reboiler, a first low-boiling column packing section, a second low-boiling column packing section, and a first condenser in sequence from bottom to top.

Preferably, the high-boiling column includes a second reboiler, a first high-boiling column packing section, a second high-boiling column packing section, a third high-boiling column packing section, and a second condenser in sequence from bottom to top.

Preferably, each packing section is provided with the extraction agent for further dissociating the associated molecules of hydrogen fluoride and chlorine trifluoride.

Preferably, the extraction agent is fluoroether oil, a mass ratio of a stationary liquid to a stationary phase in the fluoroether oil is 0.3-0.5:1, the stationary liquid is YLVACO6/16, and the stationary phase is a 401 carrier.

The present disclosure further provides a rectification method for the rectification device of electronic-grade chlorine trifluoride described above, including the following steps:

S1, controlling a temperature of a second-layer column plate at an upper end of the first reboiler to be 10° C. to 12° C., and a temperature of a second-layer column plate at a lower end of the first condenser to be −22.5° C. to 24° C.;

S2, controlling a temperature of an upper end of the second reboiler to be 11° C. to 12° C., and a temperature of a lower end of the second condenser to be −6° C. to −4° C.

The present disclosure further discloses a control system of the rectification device of electronic-grade chlorine trifluoride.

The system includes a first Hastelloy-alloy condenser 11, a first Hastelloy-alloy heating tank 12, a Hastelloy-alloy pressure-resistant heating tank 13, a three-stage metal adsorbent bed 14, a rectification device 15 of electronic-grade chlorine trifluoride, a liquefaction tank 16, and a pressure-stabilizing tank 17 connected in sequence.

Preferably, the first Hastelloy-alloy condenser 11 is configured to condense a crude chlorine trifluoride product produced in a reactor 10, which thereby generates a negative pressure by a temperature difference and provides power for outlet gas of the reactor 10; the first Hastelloy-alloy condenser 11 is configured to condense the crude chlorine trifluoride product produced in the reactor 10 to −30° C. to −50° C.

Preferably, an alkali metal adsorbent of the three-stage metal adsorbent bed 14 is heated and associated with hydrogen fluoride to form stronger hydrogen bonds for separation, so as to achieve a first-stage purification; the associated molecules of hydrogen fluoride and chlorine trifluoride are further disassociated by the two-stage cryogenic rectification device 15 to achieve a second-stage purification.

The present disclosure further discloses a purification system of electronic-grade chlorine trifluoride.

The method is a method for controlling power of the purification system of electronic-grade chlorine trifluoride by temperature difference, including the purification system of electronic-grade chlorine trifluoride, and the method including the following steps:

S1, condensing the crude chlorine trifluoride product produced in the reactor 10 by the first Hastelloy-alloy condenser 11 to form a first-stage temperature difference, which thereby provides power for the outlet gas of the reactor 10;

S2, heating the crude chlorine trifluoride product by the first Hastelloy-alloy heating tank 12, so that the liquid inside the tank is vaporized to form a second-stage temperature difference, enabling chlorine trifluoride to quickly reach a saturated vapor pressure to stop self-decomposition;

S3, heating and pressurizing the crude chlorine trifluoride product gas by the Hastelloy-alloy pressure-resistant heating tank 13 to form a third-stage temperature difference, and increasing the internal pressure of the tank to make the chlorine trifluoride gas reach a positive pressure required by subsequent purification processes such as rectification;

S4, conducting cooling and condensation by the liquefaction tank 16 to form a fourth-stage temperature difference, so that the chlorine trifluoride gas from the outlet of the rectification column is condensed into a liquid state for collection and storage.

The beneficial effects of the present disclosure are as follows: First, the reflux ratio parameter stability of a vapor-liquid (chlorine trifluoride-hydrogen fluoride) phase equilibrium system can be effectively improved by a column plate temperature control method, thus realizing wide dynamic smooth running under various working conditions; Second, the column plate temperature control method can achieve an effective separation of chlorine trifluoride and various impurity components by deep rectification technology, yielding electronic-grade chlorine trifluoride through purification.

BRIEF DESCRIPTION OF THE DRAWINGS

In order to illustrate the technical solutions of the embodiments of the present disclosure more clearly, the accompanying drawings used in the embodiments are briefly introduced. It should be understood that the following drawings only show some embodiments of the present disclosure, and thus cannot be regarded as a limitation of the scope. For those of ordinary skill in the art, other related drawings can also be obtained based on these drawings without any creative effort.

FIG. 2 is a flow chart showing a method for controlling power of a purification system of electronic-grade chlorine trifluoride by temperature difference provided in an embodiment of the present disclosure.

FIG. 3 is a flow chart showing a separation method in the purification system of electronic-grade chlorine trifluoride provided in an embodiment of the present disclosure.

FIG. 4 is a flow chart showing a rectification method in the purification system of electronic-grade chlorine trifluoride provided in an embodiment of the present disclosure.

FIGS. 5-1 to 5-6 are schematic structural diagrams showing various units used in the rectification process of a rectification column, where, FIG. 5-1 is a schematic structural diagram of an $N^{th}$-layer column plate;

FIG. 5-2 is a schematic structural diagram of a feeding plate; FIG. 5-3 is a schematic structural diagram of the bottom of column; FIG. 5-4 is a schematic structural diagram of a condenser; FIG. 5-5 is a schematic structural diagram of a reboiler; FIG. 5-6 is a cross-sectional view of the reboiler.

FIG. 6 is a schematic structural diagram of the feedforward compensation decoupling system of a rectification column;

Figure 1:
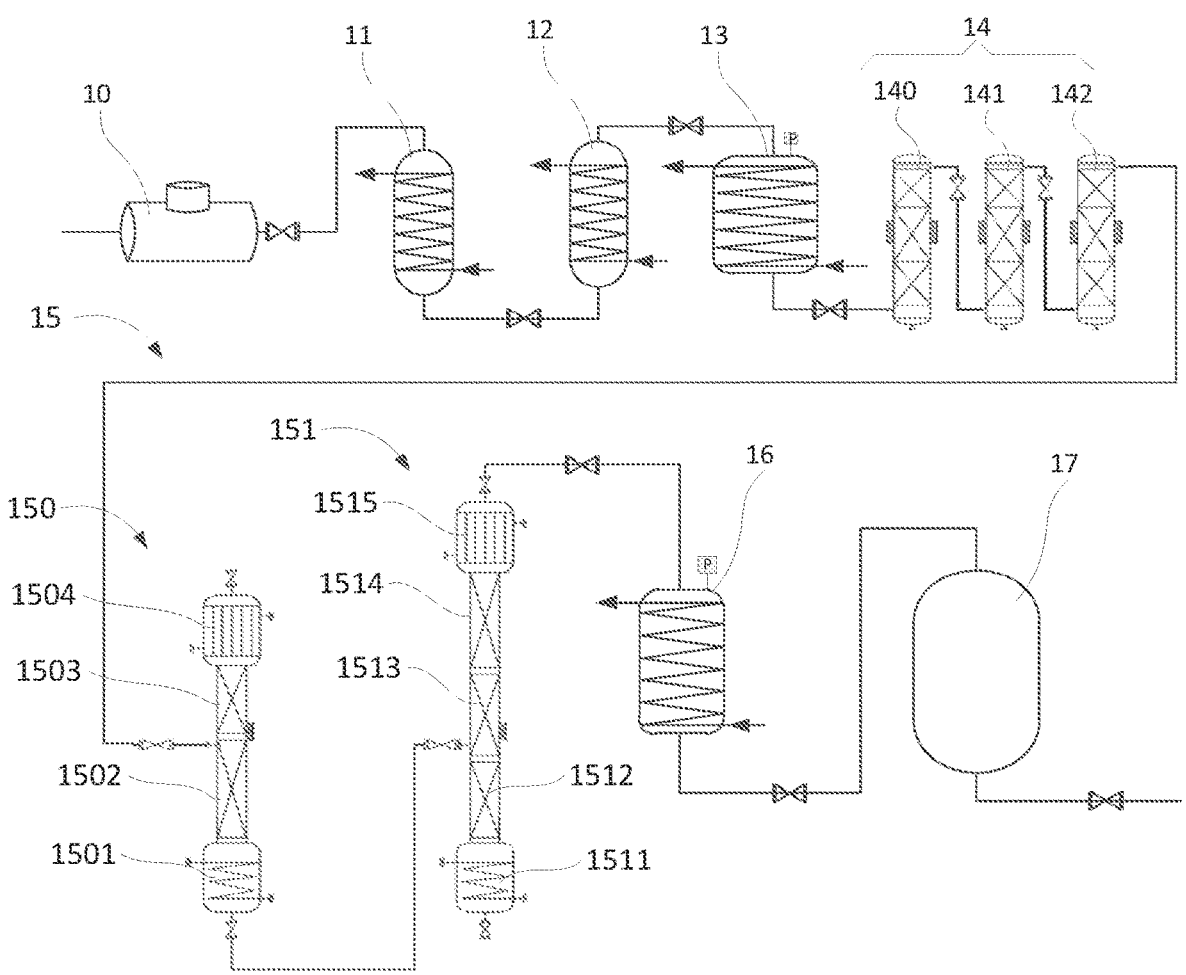
FIG. 1 is a schematic structural diagram of a purification system of electronic-grade chlorine trifluoride provided in an embodiment of the present disclosure.

where, $N_{21}(s)$ and $N_{12}(s)$ are feedforward decoupling processes.

DETAILED DESCRIPTION OF THE EMBODIMENTS

In order to make the purposes, technical solutions, and advantages of the embodiments of the present disclosure clearer, the technical solutions in the embodiments of the present disclosure will be clearly and completely described below with reference to the accompanying drawings in the embodiments of the present disclosure. Obviously, the described embodiments are some embodiments of the present disclosure, rather than all. Based on the embodiments of the present disclosure, all other embodiments obtained by those of ordinary skill in the art without creative efforts shall fall within the protection scope of the present disclosure. Therefore, the following detailed descriptions of the embodiments of the present disclosure provided in the accompanying drawings are not intended to limit the scope of the present disclosure as claimed, but merely show selected embodiments of the present disclosure. Based on the embodiments of the present disclosure, all other embodiments obtained by those of ordinary skill in the art without creative efforts shall fall within the protection scope of the present disclosure.

Embodiment 1

A rectification device of electronic-grade chlorine trifluoride includes a second-stage cryogenic rectification device, wherein the second-stage cryogenic rectification device includes a low-boiling column and a high-boiling column, and an extraction agent is arranged in the second-stage cryogenic rectification device and configured for dissociating associated molecules of hydrogen fluoride and chlorine trifluoride to meet the requirements of electronic-grade chlorine trifluoride. The low-boiling column includes a first reboiler, a first low-boiling column packing section, a second low-boiling column packing section, and a first condenser in sequence from bottom to top. The high-boiling column includes a second reboiler, a first high-boiling column packing section, a second high-boiling column packing section, a third high-boiling column packing section, and a second condenser in sequence from bottom to top. Each packing section is provided with the extraction agent for further dissociating the associated molecules of hydrogen fluoride and chlorine trifluoride.

The extraction agent is fluoroether oil, a mass ratio of a stationary liquid to a stationary phase in the fluoroether oil is 0.3-0.5:1, the stationary liquid is YLVACO6/16, and the stationary phase is a 401 carrier.

Embodiment 2

The present disclosure further provides a rectification method for the rectification device of electronic-grade chlorine trifluoride described above, the rectification device includes the technical features in Embodiment 1, and the method includes the following steps:

S1, a temperature of a second-layer column plate at an upper end of the first reboiler is controlled to be 10° C. to 12° C., and a temperature of a second-layer column plate at a lower end of the first condenser is controlled to be −22.5° C. to 24° C.;

S2, a temperature of an upper end of the second reboiler is controlled to be 11° C. to 12° C., and a temperature of a lower end of the second condenser is controlled to be −6° C. to −4° C.

Embodiment 3

Referring to FIG. 1, the present disclosure provides a purification system of electronic-grade chlorine trifluoride, including: the first Hastelloy-alloy condenser 11, the first Hastelloy-alloy heating tank 12, the Hastelloy-alloy pressure-resistant heating tank 13, the three-stage metal adsorbent bed 14, the rectification device of electronic-grade chlorine trifluoride in Embodiment 1, the liquefaction tank 16, and the pressure-stabilizing tank 17 connected in sequence.

The feeding end of the first Hastelloy-alloy condenser 11 is set at the top end thereof and in communication with the reactor 10, and the discharging end of the first Hastelloy-alloy condenser 11 is set at the bottom end thereof and connected to the feeding end of the first Hastelloy-alloy heating tank 12. The first Hastelloy-alloy condenser 11 is configured to condense a crude chlorine trifluoride product produced in the reactor 10, which thereby provides power for outlet gas of the reactor 10 through a temperature difference (generating negative pressure). The first Hastelloy-alloy condenser 11 is configured to condense the crude chlorine trifluoride product produced in the reactor 10 to −30° C. to −50° C., preferably, the first Hastelloy-alloy condenser 11 is configured to condense the crude chlorine trifluoride product produced in the reactor 10 to −35° C. to −40° C. In one embodiment, the first Hastelloy-alloy condenser 11 is configured to condense the crude chlorine trifluoride product produced in the reactor 10 to about −38° C.

The feeding end of the first Hastelloy-alloy heating tank 12 is set at the bottom thereof and in communication with the discharging end of the first Hastelloy-alloy condenser 11. The discharging end of the first Hastelloy-alloy heating tank 12 is set at the top thereof and in communication with the Hastelloy-alloy pressure-resistant heating tank 13. The first Hastelloy-alloy heating tank 12 heats the crude chlorine trifluoride product to vaporize the liquid inside the tank, quickly reaching a saturated vapor pressure to prevent self-decomposition of chlorine trifluoride. The first Hastelloy-alloy heating tank 12 heats the crude chlorine trifluoride product to 15° C. to 25° C., preferably, the first Hastelloy-alloy heating tank 12 heats the crude chlorine trifluoride product to 16° C. to 20° C. In one embodiment, the first Hastelloy-alloy heating tank 12 heats the crude chlorine trifluoride product to 18° C.

The Hastelloy-alloy pressure-resistant heating tank 13 is configured to heat and pressurize the crude chlorine trifluoride product gas, which increases the internal pressure of the tank and makes the chlorine trifluoride gas reach the positive pressure required by subsequent purification processes such as rectification. The temperature of the Hastelloy-alloy pressure-resistant heating tank 13 is 40° C. to 50° C., and the pressure of the Hastelloy-alloy pressure-resistant heating tank 13 is 0.5 MPa to 0.6 MPa. Preferably, the temperature of the Hastelloy-alloy pressure-resistant heating tank 13 is 45° C. to 48° C., and the pressure of the Hastelloy-alloy pressure-resistant heating tank 13 is 0.55 MPa to 0.58 MPa. In one embodiment, the temperature of the Hastelloy-alloy pressure-resistant heating tank 13 is 46° C., and the pressure of the Hastelloy-alloy pressure-resistant heating tank 13 is 0.56 MPa. For safety, it is necessary to control the volume of the Hastelloy-alloy pressure-resistant heating tank 13. Preferably, the volume of the Hastelloy-alloy pressure-resistant heating tank 13 is 0.5 m$^3$ to 1 m$^3$. In one embodiment, the volume of the Hastelloy-alloy pressure-resistant heating tank 13 is 0.6 m$^3$.

The three-stage metal adsorbent bed 14 includes the first alkali metal adsorbent bed 140, the second alkali metal adsorbent bed 141, and the third alkali metal adsorbent bed 142, which are configured for adsorbing free hydrogen fluoride to reduce the workload of removing hydrogen fluoride in subsequent purification. The main reason is that fluorine-hydrogen bonds are formed between hydrogen fluoride and chlorine trifluoride, leading to an increased difficulty of separation, while stronger hydrogen bonds are formed between alkali metal adsorbents of the three-stage metal adsorbent bed 14 and hydrogen fluoride by intermolecular association, assisting in separation and purification. The alkali metal adsorbent is a mixture of $Al_2O_3$ and LiF. Preferably, the alkali metal adsorbent is the mixture of $Al_2O_3$ and LiF in a mass ratio of 1:2-5. In one embodiment, the alkali metal adsorbent is the mixture of $Al_2O_3$ and LiF in a mass ratio of 1:2.4. The reaction temperature of the three-stage metal adsorbent bed 14 is 150° C. to 200° C., preferably, the reaction temperature of the three-stage metal adsorbent bed 14 is 160° C. to 180° C. In one embodiment, the reaction temperature of the metal adsorbent bed 14 is 175° C., so that the content of hydrogen fluoride in chlorine trifluoride is reduced to below 0.5 v %. The alkali metal adsorbent can be designed as spherical particles with different particle sizes ranging from 10 meshes to 200 meshes and randomly stacked in the three-stage metal adsorbent bed 14, so as to increase its surface area and improve adsorption efficiency.

The height of each alkali metal adsorbent bed may be 1.8 m to 2.5 m. In one embodiment, the height of each alkali metal adsorbent bed is about 2 m, and each alkali metal adsorbent bed can be made of a Hastelloy alloy.

In addition, since the breaking and forming of hydrogen bonds is a reversible process, the present disclosure further provides a regeneration method of the three-stage metal adsorbent bed 14. The three-stage metal adsorbent bed 14 is heated to 350° C. to 450° C. and maintained for 12 h to 96 h to facilitate the regeneration of the alkali metal adsorbent. Preferably, the three-stage metal adsorbent bed 14 is heated to 380° C. to 420° C. and maintained for 24 h to 48 h. In one embodiment, the three-stage metal adsorbent bed 14 is heated to 400° C. and maintained for 36 h.

The rectification device of electronic-grade chlorine trifluoride in Embodiment 1 is the two-stage cryogenic rectification device 15, and the rectification device includes the low-boiling column 150 and the high-boiling column 151. The low-boiling column 150 includes the first reboiler 1501, the first low-boiling column packing section 1502, the second low-boiling column packing section 1503, and the first condenser 1504 in sequence from bottom to top. The high-boiling column 151 includes the second reboiler 1511, the first high-boiling column packing section 1512, the second high-boiling column packing section 1513, the third high-boiling column packing section 1514, and the second condenser 1515 in sequence from bottom to top. An extraction agent is arranged in each packing section for further dissociating the associated molecules of hydrogen fluoride and chlorine trifluoride. The extraction agent is fluoroether oil, a mass ratio of a stationary liquid to a stationary phase in the fluoroether oil is 0.3-0.5:1, the stationary liquid is YLVAC06/16, and the stationary phase is a 401 carrier. In one embodiment, the mass ratio of the stationary liquid to the stationary phase in the fluoroether oil is 0.4:1. In order to obtain a good rectification effect, the temperature of the packing section needs to be strictly controlled. Preferably, the temperature of the second-layer column plate at the upper end of the first reboiler is 10° C. to 12° C., and the temperature of the second-layer column plate at the lower end of the first condenser is −22.5° C. to 24° C.; the temperature of the lower end of the second condenser is 11° C. to 12° C., and the temperature of the second-layer column plate at the upper end of the second reboiler is −6° C. to −4° C. The height of the first low-boiling column packing section 1502 is about 1.8 m, and the height of the second low-boiling column packing section 1503 is about 1.6 m. The height of the high-boiling column packing sections is about 2.8 m. Through the above preferred design, the content of hydrogen fluoride can be reduced to below 500 PPmv to meet the requirements of electronic-grade chlorine trifluoride.

The liquefaction tank 16, by virtue of cooling and condensation, converts the chlorine trifluoride gas from the outlet of the rectification column into a liquid state for collection and storage. The temperature of the liquefaction tank 16 is −20° C. to −30° C.

The pressure-stabilizing tank 17 is additionally provided after the liquefaction tank 16. The chlorine trifluoride liquid flows into the pressure-stabilizing tank through a pipeline and is vaporized into chlorine trifluoride gas after being heated to a predetermined temperature, and the chlorine trifluoride gas is subjected to filling after being stabilized in pressure.

Further, chlorine trifluoride, due to its special properties, is prone to reacting violently with water and other substances. In particular, it reacts violently with water to produce explosive oxyfluorides. In the present disclosure, nitrogen (low-temperature nitrogen and normal-temperature nitrogen) is used as cold and hot media of the low- and high-boiling columns, which can effectively ensure the safety during the rectification of chlorine trifluoride.

Figures 1, 5:
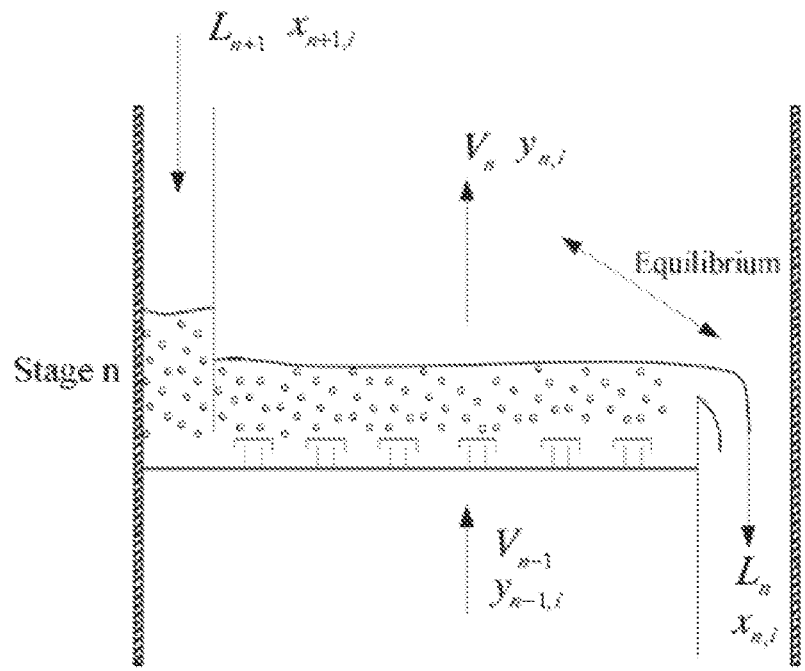
Figures 2, 5:
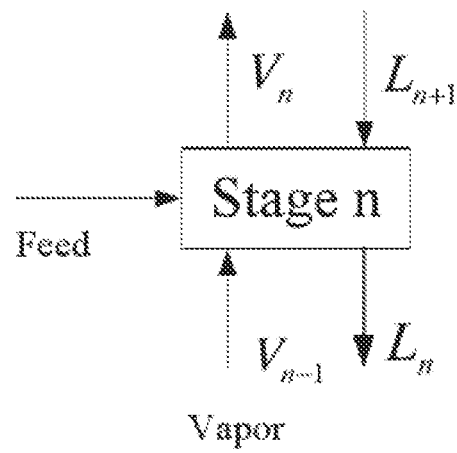

Referring to FIG. 2, the embodiment of the present disclosure further provides a method for controlling power of a purification system of electronic-grade chlorine trifluoride by temperature difference, including the following steps:

S1, the crude chlorine trifluoride product produced in the reactor 10 is condensed by the first Hastelloy-alloy condenser 11 to form a first-stage temperature difference, which thereby provides power for the outlet gas of the reactor 10. The crude chlorine trifluoride product produced in the reactor 10 is condensed by the first Hastelloy-alloy condenser 11 to −30° C. to −50° C., preferably, the crude chlorine trifluoride product produced in the reactor 10 is condensed by the first Hastelloy-alloy condenser 11 to −35° C. to −40° C. In one embodiment, the crude chlorine trifluoride product produced in the reactor 10 is condensed by the first Hastelloy-alloy condenser 11 to about −38° C.

S2, the crude chlorine trifluoride product is heated by the first Hastelloy-alloy heating tank 12, so that the liquid inside the tank is vaporized to form a second-stage temperature difference, enabling chlorine trifluoride to quickly reach a saturated vapor pressure to stop self-decomposition. The crude chlorine trifluoride product is heated by the first Hastelloy-alloy heating tank 12 to 15° C. to 25° C., preferably, the crude chlorine trifluoride product is heated by the first Hastelloy-alloy heating tank 12 to 16° C. to 20° C. In one embodiment, the crude chlorine trifluoride product is heated by the first Hastelloy-alloy heating tank 12 to 18° C.

S3, the crude chlorine trifluoride product gas is heated and pressurized by the Hastelloy-alloy pressure-resistant heating tank 13 to form a third-stage temperature difference, and the internal pressure of the tank is increased to make the chlorine trifluoride gas reach the positive pressure required by subsequent purification processes such as rectification. The temperature of the Hastelloy-alloy pressure-resistant heating tank 13 is 40° C. to 50° C., and the pressure of the Hastelloy-alloy pressure-resistant heating tank 13 is 0.5 MPa to 0.6 MPa.

S4, cooling and condensation is conducted by the liquefaction tank 16 to form a fourth-stage temperature difference, so that the chlorine trifluoride gas from the outlet of the rectification column is condensed into a liquid state for collection and storage. The temperature of the liquefaction tank 16 is −20° C. to −25° C.

Figures 3, 5:
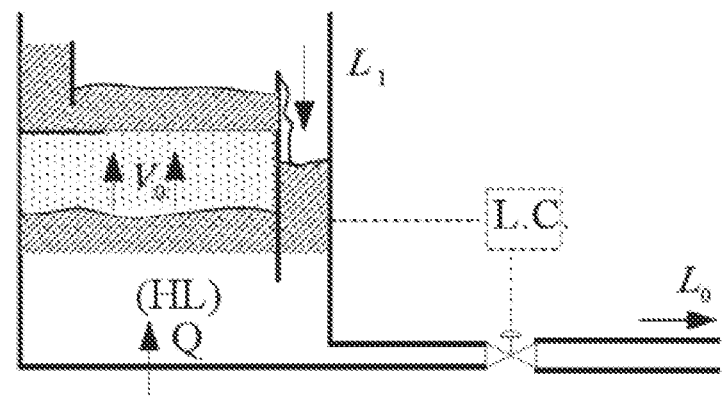

Referring to FIG. 3, the embodiment of the present disclosure further provides a separation method of electronic-grade chlorine trifluoride, including the following steps:

S5, the alkali metal adsorbent of the three-stage metal adsorbent bed 14 is heated and associated with hydrogen fluoride to form stronger hydrogen bonds for separation, so as to achieve a first-stage purification. The alkali metal adsorbent is a mixture of $Al_2O_3$ and LiF. Preferably, the alkali metal adsorbent is the mixture of $Al_2O_3$ and LiF in a mass ratio of 1:2-5. In one embodiment, the alkali metal adsorbent is the mixture of $Al_2O_3$ and LiF in a mass ratio of 1:2.4. The heating temperature of the three-stage metal adsorbent bed 14 is 150° C. to 200° C., preferably, the heating temperature of the three-stage metal adsorbent bed 14 is 160° C. to 180° C.

S6, the associated molecules of hydrogen fluoride and chlorine trifluoride are further disassociated by the two-stage cryogenic rectification device 15 to achieve a second-stage purification. The two-stage cryogenic rectification device 15 includes a fluoroether oil extraction agent. A mass ratio of a stationary liquid to a stationary phase in the fluoroether oil is 0.3-0.5:1 (preferably 0.4:1), the stationary liquid is YLVAC06/16, and the stationary phase is a 401 carrier.

Figures 4, 5:
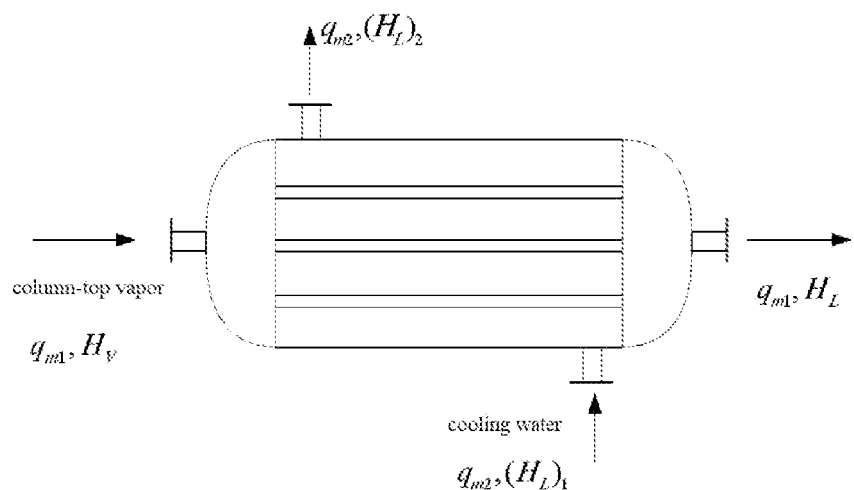
Figure 5:
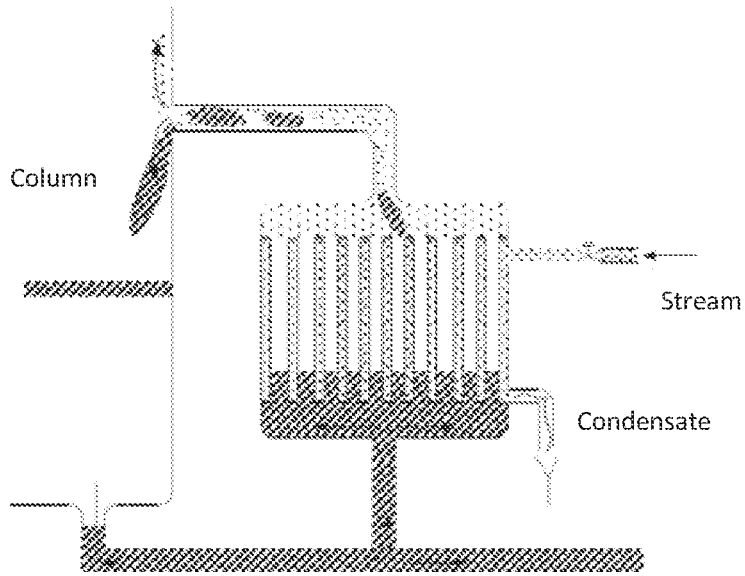

Referring to FIG. 4, the embodiment of the present disclosure further provides a method for controlling a temperature of rectification of electronic-grade chlorine trifluoride, including the following steps:

S7, the temperature of the second-layer column plate at the upper end of the first reboiler is controlled to be 10° C. to 12° C., and the temperature of the second-layer column plate at the lower end of the first condenser is controlled to be −22.5° C. to 24° C. The temperature of the column plate can be controlled by the temperatures of the hot end and the cold end.

S8, the temperature of the second-layer column plate at the upper end of the second reboiler is controlled to be 11° C. to 12° C., and the temperature of the second-layer column plate at the lower end of the second condenser is controlled to be −6° C. to −4° C. The temperature of the column plate can be controlled by the temperatures of the hot end and the cold end.

Embodiment 4

The present disclosure further discloses a control system of a rectification device of electronic-grade chlorine trifluoride. The control system is used for controlling the rectification device of electronic-grade chlorine trifluoride described in Embodiment 1 and controlling the cryogenic rectification device described in S6 of the method for controlling power of a purification system of electronic-grade chlorine trifluoride by temperature difference in Embodiment 3. The control system is specifically as follows:

The control system of the rectification device of electronic-grade chlorine trifluoride includes a two-stage cryogenic rectification device, the two-stage cryogenic rectification device includes a low-boiling column and a high-boiling column, and an extraction agent is arranged in the second-stage cryogenic rectification device and configured for disassociating the associated molecules of hydrogen fluoride and chlorine trifluoride to meet the requirements of electronic-grade chlorine trifluoride. The low-boiling column sequentially includes a first reboiler, a first low-boiling column packing section, a second low-boiling column packing section, and a first condenser from bottom to top; and the high-boiling column sequentially includes a second reboiler, a first high-boiling column packing section, a second high-boiling column packing section, and a third high-boiling column packing section, and a second condenser from bottom to top.

In the present disclosure, the "first low-boiling column packing section 1502" and the "second low-boiling column packing section 1503" of the low-boiling column, as well as the "first high-boiling column packing section 1512", the "second high-boiling column packing section 1513", and the "third high-boiling column packing section 1514" of the high-boiling column are the core parts of the rectification device. Considering common knowledges in the field and the design requirements for the technical solution of the present disclosure, all the above-mentioned "packing sections" of the present disclosure are designed to have a similar structure, each including a refining section plate, feeding plate, and a section bottom. We will elaborate on the design principle of the "packing section" below, through the detailed description of its dynamic modeling, it lays a foundation for the self-adaptive control of the rectification process in the control system of the rectification device.

Establishment of Dynamic Model of Refining Section Plate

FIG. 5-1 shows a schematic structural diagram of an $n^{th}$-layer refining section plate. The inflow material of the section plate is a liquid stream flowing from an upper section plate and a vapor stream rising from a lower section plate, and the outflow material of the section plate is a vapor stream rising toward the upper section plate and a liquid stream flowing toward the lower section plate. The difference between the inflow and outflow materials of the section plate indicates the change of a liquid retention amount of the section plate, which is expressed by the following formula per unit time:

$$\frac{dHL_n}{dt} = L_{n+1} + V_{n-1} - L_n - V_n \quad (4\text{-}1)$$

where, $HL_n$ is the liquid retention amount, $L_{n-1}$ is the liquid stream flowing from the upper section plate, $V_{n-1}$ is the vapor stream rising from the lower section plate, is the liquid stream leaving the section plate, $V_n$ is the vapor stream leaving the section plat.

A material balance calculation is conducted on the liquid phase of each component of the section plate, after the section plate reaches a vapor-liquid equilibrium, the change of the liquid phase of each component is the difference between the inflow and outflow of each component on the section plate:

$$\frac{d(HL_n \cdot x_{n,i})}{dt} = L_{n+1}x_{n+1,i} + V_{n-1}y_{n-1,i} - L_n x_{n,i} - V_n y_{n,i} \quad (4\text{-}2)$$

where, $x_{n,j}$ is a concentration of the liquid phase of component i, and $y_{n,j}$ is a concentration of the vapor phase of component i.

The above formula is subjected to differentiation and expansion to obtain the following formula:

$$\frac{dx_{n,i}}{dt} = \frac{L_{n+1}x_{n+1,i} + V_{n-1}y_{n-1,i} - x_{n,i}(L_{n+1} + V_{n-1}) - V_n(y_{n,i} - x_{n,i})}{HL_n} \quad (4\text{-}3)$$

A change rate of the concentration of the liquid phase of each component is calculated, and then combining with the concentration of the liquid phase at the current moment, the concentration the liquid phase of each component after reaching a vapor-liquid equilibrium can be obtained.

The concentration of the liquid phase of each component obtained by formula (4-3) is substituted into the phase equilibrium equation to yield the concentration of each component in the vapor stream:

$$y_{n,i} = k_{n,i} x_{n,i} \quad (4\text{-}4)$$

A verification is conducted on the calculation result by substituting into the mole fraction normalization equation:

$$\Sigma y_{n,i} = 1$$

$$\Sigma x_{n,i} = 1 \quad (4\text{-}5)$$

Enthalpy values of the vapor phase and the liquid phase of each component are obtained according to physical property data, and substituted into the heat balance equation of the section plate. That is, heat obtained by the liquid retention amount of the section plate is the difference between the heat brought by the inflow material of the section plate and the heat taken away by the outflow material of the section plate:

$$\frac{dHL_n \cdot (h_L)_n}{dt} = V_{n-1}(H_V)_{n-1} + L_{n+1}(h_L)_{n+1} - V_n(H_V)_n - L_n(h_L)_n \quad (4\text{-}6)$$

The left side of formula (4-6) is subjected to differentiation and expansion to yield the calculation expression of the vapor stream after reaching a vapor-liquid equilibrium:

$$V_n = \frac{V_{n-1}(H_V)_{n-1} + L_{n+1}(h_L)_{n+1} - (L_{n+1} + V_{n-1})(h_L)_n}{(H_V)_n - (h_L)_n} \quad (4\text{-}7)$$

Establishment of Dynamic Model of Feeding Plate

FIG. 5-2 shows a schematic structural diagram of a feeding plate. The inflow material of the feeding plate is a liquid stream flowing from an upper section plate, a vapor stream rising from a lower section plate, and a feeding stream; and the outflow material of the feeding plate is a vapor stream rising toward the upper section plate and a liquid stream flowing toward the lower section plate. The difference between the inflow and outflow materials of the feeding plate indicates the change of a liquid retention amount of the feeding plate, which is expressed by the following formula per unit time:

$$\frac{dHL_n}{dt} = L_{n+1} + V_{n-1} + F - L_n - V_n \quad (4\text{-}8)$$

F is a phase fugacity of a liquid component;

A material balance calculation is conducted on the liquid phase of each component of the feeding plate, after the feeding plate reaches a vapor-liquid equilibrium, the change of the liquid phase of each component is the difference between the inflow and outflow of each component on the feeding plate:

$$\frac{d(HL_n \cdot x_{n,i})}{dt} = L_{n+1}x_{n+1,i} + V_{n-1}y_{n-1,i} + Fx_F - L_n x_{n,i} - V_n y_{n,i} \quad (4\text{-}9)$$

The above formula is subjected to differentiation and expansion to obtain the following formula:

$$\frac{dx_{n,i}}{d} = \frac{L_{n+1}x_{n+1,i} + V_{n-1}y_{n-1,i} + Fx_F - V_n(y_{n,i} - x_{n,i}) - x_{n,i}(L_{n+1} + V_{n-1} + F)}{HL_n} \quad (4\text{-}10)$$

A change rate of the concentration of the liquid phase of each component is calculated, and then combining with the concentration of the liquid phase at the current moment, the concentration of the liquid phase of each component after reaching a vapor-liquid equilibrium can be obtained.

The concentration of the liquid phase of each component obtained by formula (4-10) is substituted into the phase equilibrium equation to yield the concentration of each component in the vapor stream:

$$y_{n,i} = k_{n,i} x_{n,i} \quad (4\text{-}11)$$

A verification is conducted on the calculation result by substituting into the mole fraction normalization equation:

$$\Sigma y_{n,i} = 1$$

$$\Sigma x_{n,i} = 1 \quad (4\text{-}12)$$

Enthalpy values of the vapor phase and the liquid phase of each component are obtained according to physical property data, and substituted into the heat balance equation of the feeding plate. That is, heat obtained by the liquid retention amount of the feeding plate is the difference between the heat brought by the inflow material of the feeding plate and the heat taken away by the outflow material of the feeding plate:

$$\frac{dHL_n \cdot (h_L)_n}{dt} = \quad (4\text{-}13)$$

$$V_{n-1}(H_V)_{n-1} + L_{n+1}(h_L)_{n+1} + Fh_F - V_n(H_V)_n - L_n(h_L)_n$$

The left side of formula (4-13) is subjected to differentiation and expansion to yield the calculation expression of the vapor stream after reaching a vapor-liquid equilibrium:

$$V_n = \frac{V_{n-1}(H_V)_{n-1} + L_{n+1}(h_L)_{n+1} + Fh_F - (L_{n+1} + V_{n-1} + F)(h_L)_n}{(H_V)_n - (h_L)_n} \quad (4\text{-}14)$$

Establishment of Mathematical Model of Section Bottom

FIG. 5-3 is a schematic structural diagram of a section bottom. After the liquid phase in the refining section enters the section bottom from top to bottom, a part of the liquid enters a reboiler and undergoes vaporization to form vapor rising and flowing back to the refining section, and another part of the liquid will be recovered as a product from the section bottom. Since the section bottom and the reboiler can be regarded as undergoing a change in the vapor-liquid equilibrium, the section bottom can also be regarded as a theoretical plate, and the stream recovered from the section bottom and the rising vapor generated by partial vaporization in the reboiler are regarded as the vapor stream and the liquid stream after reaching a vapor-liquid equilibrium.

The inflow material of the section bottom is a liquid stream $L_1$ flowing from an upper section plate, and the outflow material of the section bottom is a vapor stream $V_0$ rising toward the upper section plate and a product $L_0$ recovered from the section bottom. The difference between the inflow and outflow materials of the section bottom indicates the change $$\frac{dHL_0}{dt}$$

of a liquid retention amount of the section bottom, which is expressed by the following formula per unit time:

$$\frac{dHL_0}{dt} = L_1 - L_0 - V_0 \quad (4\text{-}15)$$

A material balance calculation is conducted on the liquid phase of each component of the section bottom, after the section bottom reaches a vapor-liquid equilibrium, the change of the liquid phase of each component is the difference between the inflow and outflow of each component on the section bottom:

$$\frac{d(HL_0 \cdot x_{0,i})}{dt} = L_1 x_{1,i} - L_0 x_{0,i} - V_0 y_{0,i} \quad (4\text{-}16)$$

The above formula is subjected to differentiation and expansion to obtain the following formula:

$$\frac{dx_{0,i}}{dt} = \frac{L_1(x_{1,i} - x_{0,i}) - V_0(y_{0,i} - x_{0,i})}{HL_0} \quad (4\text{-}17)$$

A change rate of the concentration of the liquid phase of each component is calculated, and then combining with the concentration of the liquid phase at the current moment, the concentration the liquid phase of each component after reaching a vapor-liquid equilibrium can be obtained.

The concentration of the liquid phase of each component obtained by formula (4-17) is substituted into the phase equilibrium equation to yield the concentration of each component in the vapor stream:

$$y_{0,i} = k_{0,i} x_{0,i} \quad (4\text{-}18).$$

A verification is conducted on the calculation result by substituting into the mole fraction normalization equation:

$$\Sigma y_{0,i} = 1$$

$$\Sigma x_{0,i} = 1 \quad (4\text{-}19)$$

Enthalpy values of the vapor phase and the liquid phase of each component are obtained according to physical property data, and substituted into the heat balance equation of the section bottom. That is, heat obtained by the liquid retention amount of the section bottom is the difference between the heat brought by the inflow material of the section bottom and the heat taken away by the outflow material of the section bottom:

$$\frac{dHL_0(h_L)_0}{dt} = Q + L_1(h_L)_1 - L_0(h_L)_0 - V_0(H_V)_0 \quad (4\text{-}20)$$

The left side of formula (4-20) is subjected to differentiation and expansion to yield the calculation expression of the vapor stream after reaching a vapor-liquid equilibrium:

$$Q_1 = U(T_c - T_m) \quad (4\text{-}21)$$

Hereinafter, the design of the condenser and the reboiler contained in the low-boiling column and the high-boiling column of the present disclosure is described in detail.

The condenser contains both cold and hot media for heat exchange. The heat medium is hydrocarbon gas, which rises up to the top of the condenser along the inner wall of a cylinder, enters a plate bundle, and condenses in the plate bundle. A condensate exits from an overflowing device at the bottom, and non-condensable gas is discharged from a non-condensable gas outlet on the side of equipment after passing through a gas-liquid separation device. The cold medium is cooling water, which enters the plate bundle from the lower side, and a well flow is discharged from the upper side four times, forming a cross flow with the hydrocarbon gas, taking away the latent heat and the sensible heat released by the hydrocarbon gas. The hydrocarbon gas passes through the gap between the plate bundle and the cylinder, and then rises up to the top of the plate bundle. Since a space for the flowing of the rising hydrocarbon gas is needed, an end plate cannot be used as a connection between the plate bundle and the cylinder. Therefore, In the present disclosure, a crossbeam structure is used as a main load-bearing component and placed at the bottom of the plate bundle, and a positioning device is arranged at the top to prevent the plate bundle from shaking, so that during a gas flowing process, the narrowest part becomes a space formed by a curved plate, a pressing plate, and the inner wall of the cylinder; the space must be similar in size to the space for the flowing of the gas in the plate bundle, so as not to affect the upward flowing of the gas. The space for the flowing of the gas in the plate bundle is the channel formed by plates and tubes in the axial direction of the equipment.

The hydrocarbon gas is subjected to heat exchange with the cooling water in the plate bundle, and releases the latent heat to become a liquid state after condensation. Under the action of gravity, a condensate is separated from the non-condensable gas by a baffle, and then enters an overflow pipe for reflux to the column tray. A liquid sealing device is installed at the bottom of the overflow pipe to ensure that the condensate can be smoothly discharged from the heat exchanger. Liquid discharging is the key to the normal operation of the condensing equipment. Liquid accumulation will submerge part of the plate bundle and reduce the effective heat transfer area of the heat exchanger. A certain height of liquid sealing can also prevent the hydrocarbon gas in the column from flowing back into the overflow pipe.

In order to ensure the reliability of the condenser and ensure that the two media do not contact nor leak, the equipment must be tightly sealed. The heat transfer element of the condenser is made of stainless steel sheets, and two sheets are welded by full-automatic gas tungsten arc fusion welding with argon shielding to form plates and tubes. Subsequently, several plates and tubes are welded into the plate bundle through manual argon-arc welding. Two sides of the plate bundle are clamped with thick plates, and tightened with tie rods to strengthen the pressure bearing capacity and ensure the dimension in a clamping state.

Establishment of Mathematical Model of Condenser at Column Top

FIG. 5-4 is a schematic structural diagram of a condenser at column top. The vapor phase entering the condenser at column top is condensed into a liquid, a part of which serves as a reflux liquid of the refining section, and a part of which is extracted from the top of the refining section. In the present disclosure, the condenser at column top is a shell-and-tube heat exchanger, with cooling water in the shell side and rising vapor from the refining section in the tube side, such that dividing wall type heat exchange is achieved therebetween. After the heat exchange, if the vapor phase in the tube side is completely condensed into a liquid, it is called a total condenser, and if the vapor phase in the tube side is partially condensed into a liquid, it is called a partial condenser. When the temperature of the cooling water is lower than the theoretical boiling point of vapor, it is total condensation, otherwise it is partial condensation. The condensate obtained after condensation enters the reflux tank, and then flows back to the refining section through a reflux valve.

The condenser model is mainly used to calculate the temperature of a reflux stream into the refining section, ignoring a heat exchange loss between the hot and cold fluids, it can be known from the conservation of energy that the heat reduced from the rising vapor stream at column top is equal to the heat added to the cooling water, and the heat balance equation is as follows:

$$q_{m1}H_v - q_{m1}H_L = q_{m2}(H_L)_2 - q_{m2}(H_L)_1 \quad (4\text{-}22)$$

where, $q_{m1}$ and $q_{m2}$ are mass flow rates of cold and hot fluids. An enthalpy value of the rising vapor at an inlet is calculated by the calculation formula of enthalpy value of vapor mixture:

$$H_v = \Sigma y_i((A_{vi} + B_{vi}T)T + \lambda_i) \quad (4\text{-}23)$$

An enthalpy value of the rising vapor at an outlet is calculated by the calculation formula of enthalpy value of liquid mixture:

$$H_L = \Sigma x_i(A_{Li} + B_{Li}T)T \quad (4\text{-}24)$$

Enthalpy values of the cooling water at an inlet and an outlet are calculated by the calculation formula of enthalpy value of liquid pure component:

$$H_L = (A_L + B_L T)T \quad (4\text{-}25)$$

Then, the temperature of the vapor at column top after being condensed into a liquid can be obtained.

During the structural design of the condenser of the present disclosure, it is necessary to consider factors including the parameters of a baffle, the specification and arrangement of a heat exchange tube, the total heat transfer coefficient, and the change of a tube side pressure. Hereinafter, we will elaborate on the selected parameters of the above components.

The heat transfer area determines the load capacity of the condenser and is the key to whether the equipment can perform condensation. In the present disclosure, a stainless steel sheet with rectangular corrugations is used as a heat transfer element. In general, the heat transfer coefficient of a plate heat exchanger is 2-3 times that of a traditional shell-and-tube heat exchanger, and the plate heat exchanger is more compact in structure and requires less space, which meets the requirements of a column-top condenser.

Calculation formula of heat load $Q$:
$$Q = q_{m1} c_1 \Delta t_1 = q_{m2} c_2 \Delta t_2 \tag{2-1}$$

In the formula, $q_{m1}$ and $q_{m2}$ are mass flow rates of hot and cold fluids, kg/h; $c_1$ and $c_2$ are specific heat capacities of hot and cold fluids, J/(kg·k); $\Delta t_1$ and $\Delta t_2$ are temperature differences between inlet and outlet of hot and cold fluids, ° C. Related data are substituted into formula (2-1) to obtain Q=2036.2 Kw.

Logarithmic mean temperature difference $\Delta T$ is:

$$\Delta T = \frac{(T_1 - t_2) - (T_2 - t_1)}{\ln \frac{T_1 - t_2}{T_2 - t_1}} \tag{2-2}$$

In the formula, $T_1$ and $T_2$ are temperatures of hot fluid at inlet and outlet, ° C. $T_1$=63.1° C. and $T_2$=35° C., $t_2$=35° C., and $t_1$=30° C. are substituted into formula (2-2) to obtain $\Delta T$=13.38° C.

Calculation formula of total heat transfer coefficient K is:

$$K = \frac{1}{\frac{1}{h_H} + r_1 + r_2 + \frac{1}{h_C}} \tag{2-3}$$

In the formula, $h_H$ and $h_C$ are film heat-transfer coefficients of hot and cold sides, respectively, W/(m²·K); $r_1$ and $r_2$ are thermal resistance of hot and cold sides, respectively, m²·K/W.

The film heat-transfer coefficient h can be expressed as:

$$h = c \frac{\lambda}{d} Re^m Pr^n \tag{2-4}$$

In the formula, $\lambda$ is heat conductivity coefficient, W/(m·K); d is flow diameter, m; Re is Reynolds number, Pr is Prandtl number, and c, m, and n are coefficients.

The film heat-transfer coefficients of the hot and cold sides are obtained by a well-known algorithm as: $h_H$=1356.87 W(m²·K); $h_C$=7882.37 W(m²·K), which are substituted into formula (2-3) to obtain K=689.602 W(m²·K). The heat transfer formula Q=AKΔT is used to yield the heat transfer area A=220.7 m², taking $A_0$=270 m², the area affluence is: C=$A_0$/A−1=22.3%

The baffle in the condenser of the present disclosure is designed into a horizontal circular notch shape. Generally, the height of an arcuate notch is 10%-40% of the inner diameter of the shell, and 25% is selected in the present disclosure. As such, the height of the circular notch cut is h=175 mm, and h=175 mm is selected. The dividing wall between the baffle and the inner diameter of the shell is taken as 4 mm. The spacing of the baffle is generally 0.2-1.0 times the inner diameter of the shell. Taking the spacing of the baffle as B=0.8D, then B=560 mm. The thickness of the baffle and the unsupported span can be 6 mm according to the standard. The spacing is 210 mm.

The tubes and plates of the heat exchanger are in the most common equilateral-triangle arrangement, and the tube spacing is generally a quarter of the outer diameter of the tube. The outer diameter of the tube of the present disclosure is determined to be 25 mm according to the arrangement of the commonly used tube-to-center distance in the process operation, and the corresponding center-to-center distance is 32 mm.

Establishment of Mathematical Model of Reboiler

Figures 5, 6:
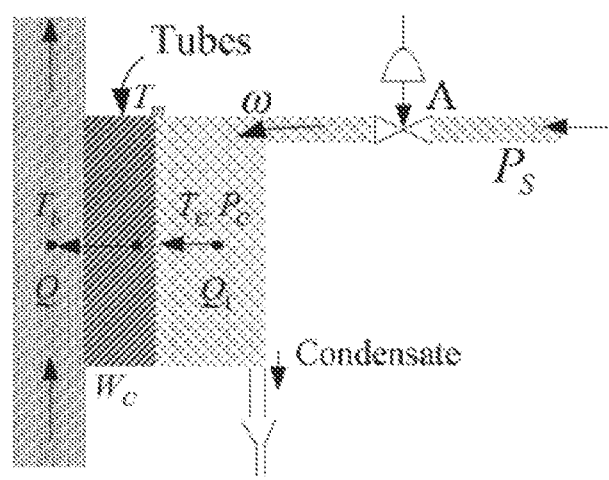
Figure 6:
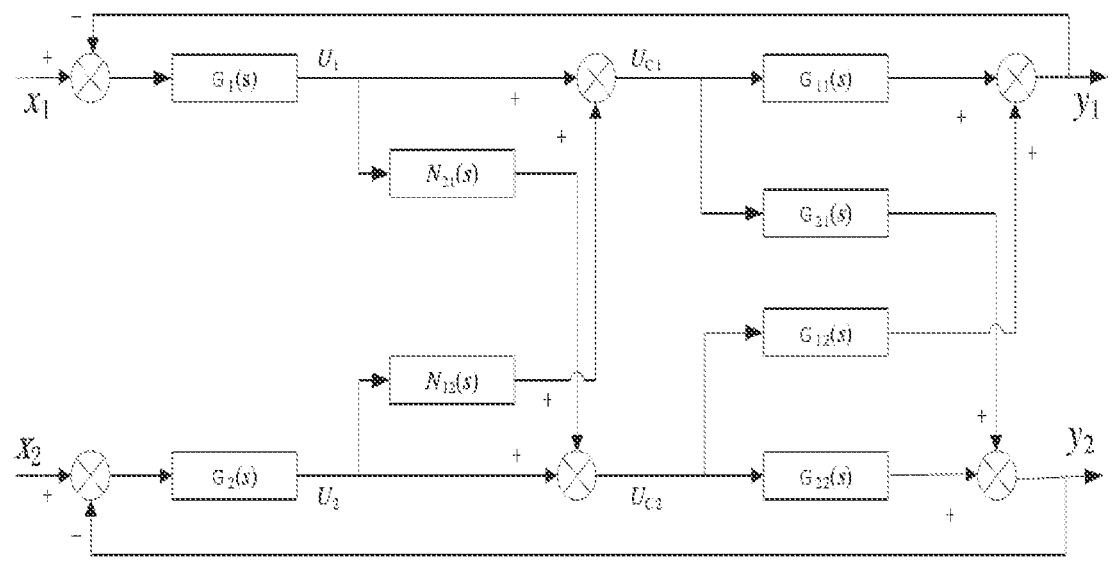

FIGS. 5-5 and 5-6 are schematic structural diagrams of a reboiler. The reboiler is a shell-and-tube heat exchanger, which generates rising vapor through vaporizing materials to provide heat for the entire rectification process. Therefore, the reboiler has a significant impact on the rectification process. The model of the reboiler is established for heat balance calculation of the heat entering the column bottom. The shell side of the reboiler allows high-pressure and high-temperature saturated vapor to pass through, and the tube side allows the materials from the refining section to pass through, such that dividing wall type heat exchange is achieved therebetween. After the heat exchange, the saturated vapor is condensed into water and discharged, and the materials from the refining section are partially vaporized and enter the refining section. Since the amount of heat transferred by the reboiler to the column has a great influence on the rectification process and the quality of the final product produced, it is necessary to control the flow rate of the saturated vapor.

The flow rate of the saturated vapor flowing toward the shell side is calculated based on vapor pressures $P_S$ and $P_C$ before and after valve, valve flow capacity $C_V$, and valve opening A:

$$\omega = AC_V \sqrt{P_S(P_S - P_C)} \tag{4-26}$$

In the above formula, $$P_C = \exp\left(C_1 + \frac{C_2}{T_C + C_3}\right) \tag{4-27}$$

where, $C_1$, $C_2$, and $C_3$ are Antoine constants

The tube temperature is calculated according to the heat transfer coefficient:

$$\frac{d}{dt}(T_m \cdot W_C) = Q_1 - Q \tag{4-28}$$

where, $T_m$ is the tube temperature, and $W_c$ is heat transfer capability.

$$Q_1 = U(T_c - T_m) \tag{4-29}$$

$$Q = U(T_m - T_b) \tag{4-30}$$

U is the heat transfer coefficient, $T_b$ is the temperature at column bottom, and $T_c$ is liquid saturation temperature.

Design Method of Reboiler:

The following steps are included: Step 1: determination of process conditions: The process conditions generally determine the flow rates, the inlet and outlet temperatures, the inlet and outlet pressures, the critical pressures, and the structure thermal resistance of a boiling medium and a heating medium. Through the process conditions, the physicochemical properties and anti-corrosion properties of the boiling and heating media can be known.

Step 2: calculation of heat load of reboiler: The heat load is calculated based on the process conditions. In general, when the flow rates and the inlet and outlet temperatures of the reboiling and heating media are given, whether the relative error of heat load of the reboiling medium and the cooling medium is less than 10% is verified, and whether the heat load of the heating medium is larger than that of the boiling medium is determined. If the above requirements are not met, it is necessary to check whether the provided process conditions are correct. In the heat transfer calculation, the heat load of the heating medium is used.

Step 3: the physical property parameters of the boiling heating fluid is determined, and the qualitative temperature and the logarithmic mean temperature difference are calculated according to the inlet and outlet temperatures of the given boiling heating medium. If a user does not give the physical property parameters, the latent heat of vaporization, density, specific heat capacity, and other physical property parameters of the boiling heating medium are calculated according to the qualitative temperature.

Step 4: calculation of structural parameters of reboiler: Whether the cold and hot fluids flow through the tube side or the shell side is determined, and the diameter of the heat exchange tube and the flow velocity in the tube are selected. According to the process conditions given and the heat intensity value of the reboiler estimated based on practical engineering experience, the heat transfer area is calculated by using a basic heat transfer equation. Considering the nature and safety factor of the preliminary estimation, the preliminarily estimated heat exchange area is generally 1.15 to 1.25 times the calculated value. Subsequently, according to the heat exchange area and referring to the standard series of reboilers, the structural parameters of the reboiler are preliminarily selected. The structural parameters mainly include: shell diameter, heat exchange tube diameter, tube length, tube center-to-center distance, total number of tubes, arrangement angle, baffle form, circular notch height, spacing, number of tube sides, shell form, and diameter of pipe for connecting tube side and shell side.

Step 5: calculation of critical maximum heat intensity: The critical maximum heat intensity and the actual heat intensity are calculated according to the process conditions and the structural parameters. If the actual heat intensity is less than 70% of the critical maximum heat intensity, and is less than 180 KJ/m³ and greater than 60 KJ/m³, it indicates that the design point is operating in the nucleate boiling region, and the preliminarily selected equipment is suitable for detailed calculation. Otherwise, the empirical heat intensity value needs to be adjusted for re-selection of a model.

Step 6: check of heat transfer performance of reboiler: The boiling heat-transfer coefficient, the film heat-transfer coefficient of the heating medium, the total heat-transfer coefficient, and the heat transfer area allowance are calculated according to the process conditions and the structural parameters. If the relative error between the calculated heat intensity and the preliminarily estimated heat intensity is greater than ±20%, the empirical value of the empirical heat intensity needs to be re-adjusted for re-selection and calculation; if the heat exchange area allowance is less than 20%, the structural parameters of the reboiler need to be re-selected.

Step 7: calculation of pressure balance and installation height: The pressure balance and installation height of the reboiler are calculated. If it does not meet design requirements, the size of equipment and the size of inlet and outlet pipelines need to be adjusted, and starting with step 5, re-selection and calculation need to be conducted until meeting the requirements.

Hereinafter, the present disclosure elaborates on key steps such as reboiler check and calculation (including heat transfer coefficient and resistance, effective mean temperature difference, heat transfer area, and installation height) according to the above steps:

Heat Transfer Coefficient

1. Boiling Heat-Transfer Coefficient of Shell Side (1) Boiling Heat-Transfer Coefficient of Bare Tube The boiling heat-transfer coefficient can be described by a dual-mechanism model, and is the sum of a nucleate boiling heat transfer coefficient and a two-phase convective heat transfer coefficient. In addition, considering that the vaporization rate of a shell-side medium in a horizontal thermosyphon reboiler is generally lower than 30%, the following formula is used to calculate the boiling heat transfer coefficient of the shell side:

$$h_o = (h_b + h_{tp}) \times 0.75 \tag{1-1}$$

where, the nucleate boiling heat transfer coefficient $h_b$:

The reboiler design is generally performed in the nucleate boiling region, and when the horizontal thermosyphon reboiler is in a fully nucleated state, the nucleate boiling coefficient is not related to fluid velocity and pressure. Since the proportion of sensible heat transfer in the nucleate boiling region is very small, an empirical value can be added to the nucleate boiling coefficient.

The film heat transfer coefficient of the nucleate boiling region outside the bare tube is calculated by the Mostinski method:

$$h_b = 1.163 \cdot \Phi \cdot \Psi \cdot Z \cdot (\Delta t)^{2.33} \tag{1-2}$$

$$\Phi = e^{-0.027(t_2 - t_1)} \tag{1-3}$$

$$\Psi = 0.714[3.28(P_t - d_0)]^m \cdot \left(\frac{1}{N_r}\right)^n \tag{1-4}$$

$$m = 0.03096 \frac{A_0 \cdot Q}{A \cdot (P_t - d_0) \cdot \Delta H_{lv}} \tag{1-5}$$

$$n = -0.24\left[1.75 + \ln\left(\frac{1}{N_r}\right)\right] \tag{1-6}$$

The formulas are available when meeting the following: $P_c > 3.0$ MPa; $(Q/A) \leq 0.9(Q/A)_{max}$; $0.001 < P_r < 0.9$.

In the formulas, $h_b$—nucleate boiling heat transfer coefficient, W/(m²·K);

$\Phi$—correction coefficient of nucleate boiling heat transfer coefficient;

$t_1$ and $t_2$—inlet and outlet temperatures of cold fluid on shell side, °C;

$\Psi$ vapor coverage correction coefficient, configured to correct the effect of vapor generated by the lower heating tube on the boiling heat transfer;

Z—function of critical pressure and contrast pressure;

$A_0$—external surface area per unit tube length, $A_0 = \pi d_0$, m²/m;

A—external surface area of reboiler heating tube, m²;

Q—heat load, W;

$\Delta H_{lv}$—latent heat of vaporization, J/kg;

$\Delta t$—temperature difference between tube wall and boiling liquid during heat transfer, °C.

$\Delta t$ is solved by the iteration method as follows: introducing variable $H_i$, letting $H_i$:

$$\frac{1}{H_i} = \frac{1}{h_{io}} + r_i\left(\frac{d_o}{d_i}\right) + r_p\left(\frac{d_o}{d_m}\right) + r_o \quad (1\text{-}7)$$

$$\frac{1}{H_i}$$

physically refers to the sum of all thermal resistance other than the thermal resistance of boiling heat transfer outside tube. The heat transfer equation:

$$h_b \cdot \Delta t = H_i \cdot (\Delta T_m - \Delta t) \quad (1\text{-}8)$$

$h_b$ in the formula is substituted into the above formula to yield:

$$[1.163 \cdot \Phi \cdot \Psi \cdot Z \cdot (\Delta t)^{2.33}] \cdot \Delta t = H_i \cdot (\Delta T_m - \Delta t) \quad (1\text{-}9)$$

It can be obtained from the above formula:

$$\Delta T_m = \frac{1.163 \Phi \Psi Z}{H_i}(\Delta t)^{3.33} + \Delta t \quad (1-10)$$

Setting the initial value of $\Delta t$: $\Delta t = 0.5 \cdot (T_D - t_D)$
The $m^{th}$ iteration value:

$$\Delta T'_m = \frac{1.163 \cdot \Phi \cdot \Psi \cdot Z}{H_i}(\Delta t)^{3.33} + \Delta t$$

When $|\Delta T_m' - \Delta T_m| \leq 0.1°$ C., the iteration is completed; otherwise letting $\Delta t = \Delta t + (\Delta T_m' - \Delta T_m) \times 0.1$ and substituting into the formula again for calculation until convergence, so as to obtain $\Delta t$.

The two-phase convective heat transfer coefficient:

$$h_p = F_B \cdot h_t \quad (1\text{-}11)$$

Shell-side two-phase convective factor: $F_B = 2.17 \times (X_n^{-1})^{0.7}$
When $F_B > 2.5$, letting $F_B = 2.5$.
In the formula, $h_l$—convective heat transfer coefficient calculated according to the entire liquid phase, W/(m²·K);
$h_{tp}$—two-phase convective heat transfer coefficient; W/(m²·K).

(2) T-Shaped Finned Tube- and Shell-Side Boiling Heat Transfer Coefficient

During the manufacture of the T-shaped finned tube, the parameters that need to be adjusted are the pitch and the opening between fins. In general, the commonly used pitch is between 1 mm and 3 mm, the opening between the fins is between 0.15 mm and 0.55 mm, and the height of the fin is between 0.9 mm and 1.2 mm. The commonly used tube parameters are shown in the table.

The boiling heat transfer coefficient outside the T-shaped finned tube is calculated by the following formulas:

$$h_{tp} = C \cdot \lambda_l X_1^{2.4\%} \cdot X_2^{-0.7955} \cdot X_3^{0.3327} \cdot X_4^{-0.699} \cdot Pr_l^{0.3} \quad (1\text{-}12)$$

$$X_1 = \frac{\rho_v \cdot \mu_l}{\rho_l \cdot \mu_v} \quad (1\text{-}13)$$

$$X_2 = \frac{q \cdot d_o}{\mu_l \cdot \Delta H_{lv}} \quad (1\text{-}14)$$

$$X_3 = \frac{\sigma}{\rho_l} \quad (1\text{-}15)$$

$$X_4 = \frac{\sigma \cdot \rho_v \cdot \Delta H_{lv}^2}{q^2} \quad (1\text{-}16)$$

In the formulas, C—constant related to the structure of the T-shaped tube, $C = 1.47 \times 10^{12}$, suitable for 30T018-2000 series;
$\lambda_l$—liquid phase thermal conductivity, W/(m·° C.);
$X_1, X_2, X_3, X_4$—parameters;
$Pr_l$—liquid Prandtl number;
q—average heat intensity based on the outer surface area of bare pipe, W/m²;
σ—liquid phase surface tension, N/m;
$\mu_l$—liquid phase dynamic viscosity, Pa·s;
$\mu_v$—vapor phase dynamic viscosity, Pa·s;
$\rho_l$—vapor phase viscosity, kg/m³;
If water vapor is used as the heating medium in the tube, the following empirical formulas can be used for calculation:

$$h_{io} = (7956.2 + 3.5803 Re_i^{0.8}) \cdot \frac{d_i}{d_o} \quad (1\text{-}16)$$

$$Re_i = \frac{d_i \cdot G_i}{\mu_l} \quad (1\text{-}17)$$

$$G_i = \frac{W_i}{S_i} \quad (1\text{-}18)$$

In the formulas, $Re_i$—Reynolds number of the medium in the tube;
$G_i$—total mass flow rate, kg/(m²·s);
$S_i$—tube-side flow area, m²;
Pressure balance and installation height:
When designing the reboiler, it is necessary to carry out the shell-side pressure balance calculation to determine the elevation difference between the refining section and the reboiler and various installation dimensions of the reboiler to ensure the normal circulation of the reboiler during operation.
(1) Friction Loss of Reboiler Inlet Line $$\Delta P_1 = \frac{f_1 \cdot u_1^2 \cdot L_1}{19.62 d_1} \quad (1\text{-}19)$$

| Tube size | Fin outer diameter | Tube inner diameter | Fin root diameter | Fin spacing | Tunnel width | Average opening | Fin height | Minimum tube thickness | Bare tube length |
|---|---|---|---|---|---|---|---|---|---|
| d × δ | $d_{of}$ | $d_i$ | $d_r$ | t | 2a | b | h | $\delta_{max}$ | l |
| 19 × 2.0 | 18.2 | 13.0 | 16.0 | 1.6 | 0.5 | 0.2-0.4 | 0.9-1.2 | 1.5 | 130 |
| 25 × 25 | 24.2 | 180 | 22.0 | 1.6 | 0.7 | 0.2-0.4 | 0.9-1.2 | 2.0 | 130 |

In the formula, $\Delta P_1$—pressure drop of reboiler inlet line, m liquid column;
$\mu_1$—flow rate at inlet tube, m/s;
$d_1$—inner diameter of inlet tube, m;
$L_1$—equivalent diameter from column bottom to reboiler inlet line, including the length of the straight tube part of the inlet line, shrinkage of liquid out of column, expansion of liquid entering reboiler, and equivalent lengths of tube members such as valve, elbow nozzle, m;
$f_1$—friction coefficient of inlet line.

$$Re_1 = \frac{d_1 \cdot G_1}{\mu_1} \tag{1-20}$$

$$G_1 = \frac{W_o}{S_1} \tag{1-21}$$

$$S_1 = 0.785 \times d_1^2 \tag{1-22}$$

When $Re_1 \leq 1000$, $f_1 = 67.63 Re_1^{-0.9873}$
When $1000 < Re_1 < 4000$, $f_1 = 0.496 Re_1^{-0.2653}$
When $Re_1 \geq 4000$, $f_1 = 0.344 Re_1^{-0.2258}$
In the formulas, $G_1$—mass flow rate of inlet tube, kg/(m²·s);
$S_1$—flow area of inlet line, m².

(2) Friction Loss of Reboiler Outlet Line $$\Delta P_2 = \frac{f_2 \cdot u_2^2 \cdot L_2 \cdot \rho_{lv}}{19.62 d_2 \cdot \rho_l} \tag{1-23}$$

$$Re_2 = \frac{d_2 \cdot u_2 \cdot \rho_{lv}}{\mu_{lv}} \tag{1-24}$$

$$\rho_{lv} = \frac{1}{\frac{y}{\rho_v} + \frac{1-y}{\rho_l}} \tag{1-25}$$

$$\mu_{lv} = \frac{1}{\frac{y}{\mu_v} + \frac{1-y}{\mu_l}} \tag{1-26}$$

In the formulas, $\Delta P_2$—pressure drop of reboiler outlet line, m liquid column;
$f_2$—friction coefficient of outlet line;
$d_2$—diameter of inlet line, m;
$L_1$—equivalent diameter of pipeline from reboiler outlet to column inlet, including the length of the straight tube part of the outlet line, shrinkage of liquid out of reboiler, expansion of liquid entering column, and equivalent lengths of tube members such as valve, elbow nozzle, m;
$\rho_{lv}$—average density of vapor-liquid mixture in the outlet tube, kg/m³;
$\mu_{lv}$—average viscosity of vapor-liquid mixture in the outlet tube, Pa·s.

(3) Hydrostatic Head of Shell Side of Reboiler $$\Delta P_3 = D_s \cdot \frac{\overline{\rho}}{\rho_l} \tag{1-27}$$

$$\overline{\rho} = \frac{\rho_l + \rho_{lv}}{2} \tag{1-28}$$

In the formulas, $\Delta P_3$—hydrostatic head in the reboiler, m liquid column;
$\overline{\rho}$—average density, kg/m³;
$D_s$—shell diameter of reboiler, m.

(4) Hydrostatic Head in Reboiler Outlet Line $$\Delta P_4 = (H_1 + H_2 + H_x) \cdot \left(\frac{\rho_{lv}}{\rho_l}\right) \tag{1-29}$$

In the formula, $\Delta P_4$—hydrostatic head of outlet line, m liquid column;
$H_1$, $H_2$, and $H_x$—elevation difference (5) Frictional Pressure Drop of Shell Side of Reboiler $$\Delta P_5 = \frac{D_s \cdot (N_B + 1) \cdot f_5 \cdot G_s^2}{39.24 d_e \cdot \rho_l \cdot \overline{\rho}} \tag{1-30}$$

$$Re_0 = \frac{d_e \cdot G_s}{\mu_l} \tag{1-31}$$

In the formulas, $\Delta P_5$—pressure drop of shell side, m liquid column;
$N_B$—number of baffles;
$d_e$—equivalent diameter of tube, m;
$G_s$—mass flow rate of shell side, setting flow rate of horizontal thermosyphon reboiler as half of total flow rate, kg/(m²·s);
$f_5$—friction coefficient of shell side.
When $1.0 \leq Re_o < 10$, $f_5 = 98 \cdot Re_o^{-0.99}$
When $100 \leq Re_o < 1.5 \times 10^3$, $$f_5 = 0.8466\left(0.402 + \frac{3.1}{Re_o} + \frac{3.5102 \times 10^4}{Re_o^2} - \frac{6.85 \times 10^6}{Re_o^3} + \frac{4.157 \times 10^8}{Re_o^4}\right)$$

When $1.5 \times 10^3 \leq Re_o < 1.5 \times 10^4$, $f_5 = 0.6179 \cdot Re_o^{-0.0774}$
When $1.5 \times 10^4 \leq Re_o < 10^6$, $f_5 = 1.2704 \cdot Re_o^{-0.153}$ (6) Installation Height of Reboiler
The installation height refers to the elevation difference between the bottom of the column and the top of the reboiler, which can be obtained from the principle of pressure balance:

$$(H_1 + H_x + D_s) - \Delta P_1 = \Delta P_2 + \Delta P_3 + \Delta P_4 + \Delta P_5 \tag{1-32}$$

letting: $\Delta P_\Sigma = \Delta P_1 + \Delta P_2 + \Delta P_3 + \Delta P_4 + \Delta P_5$ substituting into the formula to obtain: $H_x = \Delta P_\Sigma - D_s - H_l$ vertical length of reboiler outlet line is: $H = H_1 + H_2 + H_x$ (1-33)

equivalent length of reboiler inlet line is: $L_1 = L_{1o} + H_x$ (1-34)

equivalent length of reboiler outlet line is: $L_2 = L_{2o} + H_x$ (1-35)

calculation is conducted on all the above formulas to obtain H.

The reboiler adopts a horizontal double-tube side heat exchanger. A partition is set between the inlet and outlet seals of a heat medium. The end of T-shaped fin is welded on the tube plate of a heat exchange tube. When the heat exchange tube splits, the seal flange can be removed to take out the tube plate together with the heat exchange tube, which is convenient for maintenance and replacement. Compared with traditional tubular heat exchangers, since it is difficult for maintenance when a traditional tubular heat exchanger splits and the only way is to block two ends of the heat exchange tube to remedy heat exchange area loss, this improvement can realize replacement of a broken heat exchange tube without cause heat exchange area loss, reduce maintenance time, and improve production efficiency. The seal partition can also prolong the time of the heat medium staying in the reboiler, which is conducive to sufficient heat exchange with materials in the reboiler, improving efficiency and reducing energy consumption.

The Control Process and Control Principle of Rectification in the Refining Section are as Follows:

According to the principle of recitification and thermodynamic properties, when the pressure in the refining section is constant, there is a certain functional relationship between the temperature and the composition. Considering that it is difficult to perform an on-line measurement of the properties of output components, at present, the main means to control both ends during a rectification process is to indirectly acquire the properties of output components by temperature measurement. That is, the reflux volume at the top of the refining section is used to control the temperature at the top of the refining section, and the heating amount at the bottom of the refining section is used to control the temperature at the bottom of the refining section, such that the purpose of controlling product quality is achieved.

The control components of the refining section in the present disclosure include the following parts:

scale regulator: Model: DTZ-2100, the regulator performs proportion integration differentiation on the difference between a received signal and a given signal, controls an actuator with current output, and can automatically adjust parameters such as temperature, pressure, and flow at the same time.

temperature transmitter: K-type nickel-chromium nickel-silicon thermocouple is selected as a temperature sensor, and KBW-1121 is selected as a temperature transmitter in the present disclosure, which has a wide operating temperature range and stable performance at high temperature, as well as having an approximately linear relation between thermo-electromotive force and temperature, and thus suitable for continuous use in oxidizing and inert atmospheres. The upper limit of the temperature is 1200° C. for short-term use and 1000° C. for long-term use. The input signal of KBW-1121 should not be less than 3 mV when it is in a small rangeability, and should be less than 80 mV when it is in a large rangeability. The output signal of KBW-1121 is 1 V to 5 V DC or 4 mA to 20 mA ADC. The load resistance is 0Ω to 500Ω. When the rangeability is not less than 5 mV, the accuracy of KBW-1121 is ±0.5%. When the rangeability is 3 mV to 5 mV, the accuracy of KBW-1121 is ±1.0%. The temperature of the operating environment of KBW-1121 is 5° C. to 40° C., and the relative humidity of the operating environment is 10% to 75%.

flow transmitter: since the medium that needs to detect the flow is heated water vapor, a differential transmitter is selected.

electric-pneumatic valve positioner: ZPD-2000 series electric-pneumatic valve positioner is selected. The main performance indicators are as follows: the input signal has six ranges, 4 mA to 20 mA, 4 mA to 12 mA, 12 mA to 20 mA, 0 mA to 10 mA, 0 mA to 5 mA, and 5 mA to 10 mA; the output pressure is 0.02 MPa to 0.5 MPa. The rated stroke has two types of linear stroke and angular stroke, of which the linear stroke has a range of 10 mm to 100 mm, and the angular stroke has three ranges of 0° to 50°, 0° to 70°, and 0° to 90°. The air source pressure is 0.14 MPa to 0.55 MPa. When the input signal is between 4 mA and 20 mA, the input impedance is 300Ω, and when the input signal is between 0 mA and 10 mA, the input impedance is 1000Ω.

electric regulating valve: Model: QSVP-16K, the working power is single-phase 220 V, the control signal is 4 mA to 20 mA or 1 V-5 V DC, and the output is the valve position signal of 4 mA-20 mA DC.

According to the process and production requirements of the rectification, in order to ensure the stable production of system, the present disclosure uses the incremental digital proportion integration differentiation as the control algorithm of the controller to realize the dynamic control of the rectification process in the refining section. The incremental digital proportion integration differentiation control algorithm realizes the control with increment $\Delta u(k)$ as the control quantity. The calculation equation is as follows:

$$u(k)=u(k-1)+k_p(e(k)-e(k-1))+k_i e(k)+k_d(e(k)-2e(k-1)+e(k-2))$$

Incremental type is to add a variable to the actual value of the original output. Only when a deviation occurs, will the output incremental value be generated, which can not only avoid the adverse effects caused by the accumulation of deviation, but also easily realize the undisturbed switching from manual to automatic, thus ensuring the stability of system.

In order to facilitate the further study of the temperature control system of the refining section, in view of the control characteristics of the temperature system of the refining section and the main influencing factors of variables in the system, and based on characteristics such as the mechanism relationship and thermodynamic static equation of the above-mentioned refining section dynamic mathematical model, the existing nonlinearity of temperature system, system time delay caused by fluid transfer and energy transfer, and strong coupling and time-varying characteristics of temperatures at both ends, the present disclosure select a steady-state operating point in the temperature system of the refining section, and derive its approximate mathematical model under this operating state, as shown in the following formula:

$$G(s) = \begin{bmatrix} \dfrac{4.12e^{-5.5s}}{12.7s+1} & \dfrac{1.87e^{-1.2s}}{14.7s+1} \\ \dfrac{1.34e^{-5s}}{10.2s+1} & \dfrac{0.93e^{-1.5s}}{8.2s+1} \end{bmatrix} \quad (4\text{-}1)$$

According to the coupling characteristics of the dual-input dual-output system structure, the feedforward compensation decoupling system is designed with the structure shown in FIG. 6. To achieve decoupling, the following can be obtained according to the invariance principle:

$$U_1(s)G_{21}(s)+U_1(s)N_{21}(s)G_{22}(s)=0$$

$$U_2(s)G_{12}(s)+U_2(s)N_{12}(s)G_{11}(s)=0 \quad (4\text{-}2)$$

$N_{21}(s)$ and $N_{12}(s)$ are feedforward decoupling processes. The mathematical model of the feedforward decoupling processes can be obtained from the above formula as:

$$\begin{cases} N_{21}(s) = -\dfrac{G_{21}(s)}{G_{22}(s)} \\ N_{12}(s) = -\dfrac{G_{12}(s)}{G_{11}(s)} \end{cases} \quad (4\text{-}3)$$

Substituting formula (4-1) into formula (4-3), the decoupler transfer functions of the refining section system can be respectively obtained as:

$$N_{21}(s) = -\frac{10.99s + 1.34}{10.1s + 0.93} e^{-3.5s}$$

$$N_{12}(s) = -\frac{23.75s + 1.87}{60.42s + 4.12} e^{-4.2s}$$

After the actual verification of the system, the specific control parameters under the condition of feedforward decoupling are as follows: the parameters of the temperature controller at the bottom of the refining section are: $k_p$=0.508, $k_i$=0.041, $k_d$=0.201

The parameters of the temperature controller at the top of the refining section are: $k_p$=0.421, $k_i$=0.201, $k_d$=0.189

The following disturbances are applied to the system:

① When t=400, a temperature disturbance with a disturbance signal of +10% is applied to the top loop of the refining section to detect the decoupling capability of the bottom loop of the refining section;

② When t=600, a temperature disturbance with a disturbance signal of +10% is applied to the bottom loop of the refining section to detect the decoupling capability of the top loop of the refining section.

By comparing with the dynamic response results of the system under the conventional proportional, integral, and differential controllers, those skilled in the art reach the following conclusions: the overshoot of the control system of the refining section after feedforward compensation decoupling has been reduced to some extent, and the adjustment time of suppressing feeding disturbance is shortened. At 400 s and 600 s, a step disturbance is applied to the reflux flow at the top of the refining section and the heating amount at the bottom of the refining section, respectively. Under the feedforward decoupling control, not only can the disturbance of the current loop be effectively suppressed, but also the influence on the other loop can be effectively avoided. Compared with the traditional control results, the decoupling effect is very remarkable.

The present disclosure realizes the precise design of the rectification device and the precise control of the rectification process by modeling the rectification device, which can effectively improve the reflux ratio parameter stability of a vapor-liquid (chlorine trifluoride-hydrogen fluoride) phase equilibrium system, thus realizing wide dynamic smooth running under various working conditions. The present disclosure can achieve an effective separation of chlorine trifluoride and various impurity components by deep rectification technology, yielding electronic-grade chlorine trifluoride through purification.

The foregoing shows and describes the basic principles, main features and advantages of the present disclosure. It should be understood by those skilled in the art that the present disclosure is not limited by the above-mentioned embodiments. The above-mentioned embodiments and descriptions only illustrate the principles of the present disclosure. Without departing from the spirit and scope of the present disclosure, there will be various variations and improvements, which all fall within the scope of the claimed invention. The scope of protection to be claimed by the present disclosure is defined by the appended claims and their equivalents.

What is claimed is:

1. A rectification method for a rectification device of electronic-grade chlorine trifluoride, comprising a rectification device of electronic-grade chlorine trifluoride which comprises a two-stage cryogenic rectification device, wherein an extraction agent is arranged in the two-stage cryogenic rectification device and configured for dissociating associated molecules of hydrogen fluoride and chlorine trifluoride; and the extraction agent is fluoroether oil, a mass ratio of a stationary liquid to a stationary phase in the fluoroether oil is 0.3-0.5:1, and the stationary liquid is YLVACO6/16, wherein the two-stage cryogenic rectification device comprises a low-boiling column, and the low-boiling column comprises a first reboiler, a first low-boiling column packing section, a second low-boiling column packing section, and a first condenser in sequence from bottom to top; the two-stage cryogenic rectification device comprises a high-boiling column, and the high-boiling column comprises a second reboiler, a first high-boiling column packing section, a second high-boiling column packing section, a third high-boiling column packing section, and a second condenser in sequence from bottom to top, characterized by comprising the following steps:

S1, controlling a temperature of a second-layer column plate at an upper end of the first reboiler to be 10° C. to 12° C., and a temperature of a second-layer column plate at a lower end of the first condenser to be −22.5° C. to 24° C.; wherein the temperature of the column plate can be controlled by temperatures of a hot end and a cold end;

S2, controlling a temperature of an upper end of the second reboiler to be 11° C. to 12° C., and a temperature of a lower end of the second condenser to be −6° C. to −4° C.; wherein the temperature of the column plate can be controlled by the temperatures of the hot end and the cold end.

2. A control method for a purification system of electronic-grade chlorine trifluoride, comprising a purification system of electronic-grade chlorine trifluoride, wherein the purification system of electronic-grade chlorine trifluoride comprises a first Hastelloy-alloy condenser, a first Hastelloy-alloy heating tank, a Hastelloy-alloy pressure-resistant heating tank, a three-stage metal adsorbent bed, a rectification device of electronic-grade chlorine trifluoride, a liquefaction tank, and a pressure-stabilizing tank connected in sequence, wherein the rectification device of electronic-grade chlorine trifluoride: comprises a two-stage cryogenic rectification device, an extraction agent is arranged in the two-stage cryogenic rectification device and configured for dissociating associated molecules of hydrogen fluoride and chlorine trifluoride; and the extraction agent is fluoroether oil, a mass ratio of a stationary liquid to a stationary phase in the fluoroether oil is 0.3-0.5:1, and the stationary liquid is YLVACO6/16, an alkali metal adsorbent of the three-stage metal adsorbent bed is heated and associated with hydrogen fluoride to form stronger hydrogen bonds for separation, so as to achieve a first-stage purification, the associated molecules of hydrogen fluoride and chlorine trifluoride are further disassociated by the two-stage cryogenic rectification device to achieve a second-stage purification; the two-stage cryogenic rectification device comprises a low-boiling column, and the low-boiling column comprises a first reboiler, a first low-boiling column packing section, a second low-boiling column packing section, and a first condenser in sequence from bottom to top; the two-stage cryogenic rectification device comprises a high-boiling column, and the high-boiling column comprises a second reboiler, a first high-boiling column packing section, a second high-boiling column packing section, a third high-boiling column packing section, and a second condenser in sequence from bottom to top; and further comprising a rectification method for the rectification device of electronic-grade chlorine trifluoride, a method for controlling power of the purification system of electronic-grade chlorine trifluoride by temperature difference, and a separation method in the purification system of electronic-grade chlorine trifluoride, wherein the rectification method for the rectification device of electronic-grade chlorine trifluoride comprises the following steps: S1, controlling a temperature of a second-layer column plate at an upper end of the first reboiler to be 10° C. to 12° C., and a temperature of a second-layer column plate at a lower end of the first condenser to be −22.5° C. to 24° C.; wherein the temperature of the column plate can be controlled by temperatures of a hot end and a cold end; S2, controlling a temperature of an upper end of the second reboiler to be 11° C. to 12° C., and a temperature of a lower end of the second condenser to be −6° C. to −4° C.; wherein the temperature of the column plate can be controlled by the temperatures of the hot end and the cold end; characterized in that:

the method for controlling power of the purification system of electronic-grade chlorine trifluoride by temperature difference comprises the following steps:

S1, condensing the crude chlorine trifluoride product produced in the reactor by the first Hastelloy-alloy condenser to form a first-stage temperature difference, which thereby provides power for the outlet gas of the reactor; wherein the crude chlorine trifluoride product produced in the reactor is condensed by the first Hastelloy-alloy condenser to −30° C. to −50° C.;

S2, heating the crude chlorine trifluoride product by the first Hastelloy-alloy heating tank, so that the liquid inside the tank is vaporized to form a second-stage temperature difference, enabling chlorine trifluoride to quickly reach a saturated vapor pressure to stop self-decomposition; wherein the crude chlorine trifluoride product is heated by the first Hastelloy-alloy heating tank to 1555° C. to 25° C.;

S3, heating and pressurizing the crude chlorine trifluoride product gas by the Hastelloy-alloy pressure-resistant heating tank to form a third-stage temperature difference, and increasing the internal pressure of the tank to make the chlorine trifluoride gas reach a positive pressure required by subsequent purification processes such as rectification;

S4, conducting cooling and condensation by the liquefaction tank to form a fourth-stage temperature difference, so that the chlorine trifluoride gas from the outlet of the rectification column is condensed into a liquid state for collection and storage; wherein a temperature of the Hastelloy-alloy pressure-resistant heating tank is 40° C. to 50° C., and a pressure of the Hastelloy-alloy pressure-resistant heating tank is 0.5 MPa to 0.6 MPa;

the separation method in the purification system of electronic-grade chlorine trifluoride comprises the following steps:

S5, heating the alkali metal adsorbent of the three-stage metal adsorbent bed, and enabling the alkali metal adsorbent to be associated with hydrogen fluoride to form stronger hydrogen bonds for separation, so as to achieve a first-stage purification; wherein the alkali metal adsorbent is a mixture of $Al_2O_3$ and LiF; a heating temperature of the three-stage metal adsorbent bed is 150° C. to 200° C.;

S6, further disassociating the associated molecules of hydrogen fluoride and chlorine trifluoride by the two-stage cryogenic rectification device to achieve a second-stage purification; wherein fluoroether oil in the two-stage cryogenic rectification device is the extraction agent, a mass ratio of a stationary liquid to a stationary phase in the fluoroether oil is 0.4:1, the stationary liquid is YLVAC06/16, and the stationary phase is a 401 carrier.

* * * * *